United States Patent [19]

Cianci

[11] Patent Number: 4,946,451

[45] Date of Patent: Aug. 7, 1990

[54] LIQUID VALVE SYSTEM

[75] Inventor: James P. Cianci, Cary, Ill.

[73] Assignee: The Kendall Company, Boston, Mass.

[21] Appl. No.: 825,840

[22] Filed: Feb. 4, 1986

Related U.S. Application Data

[63] Continuation of Ser. No. 682,993, Dec. 18, 1984, abandoned, which is a divisional of Ser. No. 461,351, Jan. 27, 1983, Pat. No. 4,526,576.

[51] Int. Cl.⁵ .............................................. A61M 1/00
[52] U.S. Cl. ................................... 604/323; 604/335; 604/350; 137/855
[58] Field of Search ........................... 137/38, 43, 855; 604/322-325, 335, 350; 128/760, 762, 766, 767, DIG. 24

[56] References Cited

U.S. PATENT DOCUMENTS

| | | | |
|---|---|---|---|
| 1,955,733 | 4/1934 | Bijur | 137/855 |
| 2,001,885 | 5/1935 | Ohmart | 137/855 |
| 3,529,599 | 9/1970 | Folkman et al. | 604/323 |
| 3,586,041 | 1/1970 | Monetere | 604/323 |
| 4,059,124 | 11/1977 | Hill | 137/38 |
| 4,305,403 | 12/1981 | Dunn | 604/323 |
| 4,512,770 | 4/1985 | Cianci et al. | 604/323 |

*Primary Examiner*—Jerome L. Kruter
*Attorney, Agent, or Firm*—Powell L. Sprunger

[57] ABSTRACT

A liquid drainage system comprising a receptacle having a front wall, a back wall, and a chamber for collection of liquid therein. The system has a housing secured to an upper portion of the receptacle, said housing having a drip chamber, an annular wall in a lower portion of the drip chamber defining a valve seat, with said seat being disposed at an acute angle relative to the horizontal when the receptacle is in an upright position. The system has an anti-reflux valve comprising a sheet of flexible material having an upper portion and a lower portion and extending across said drip chamber such that the sheet is sufficiently large to engage against said seat peripherally around the drip chamber. The system has a device for retaining an upper portion of the valve against an upper portion of the seat, said valve being sufficiently flexible such that a lower portion of the valve flexes away from the seat when the receptacle is placed in an upright position due to gravity in the absence of liquid adjacent said valve and seat, and said lower portion of the valve flexes against the seat when the receptacle is disposed in a horizontal position.

6 Claims, 2 Drawing Sheets

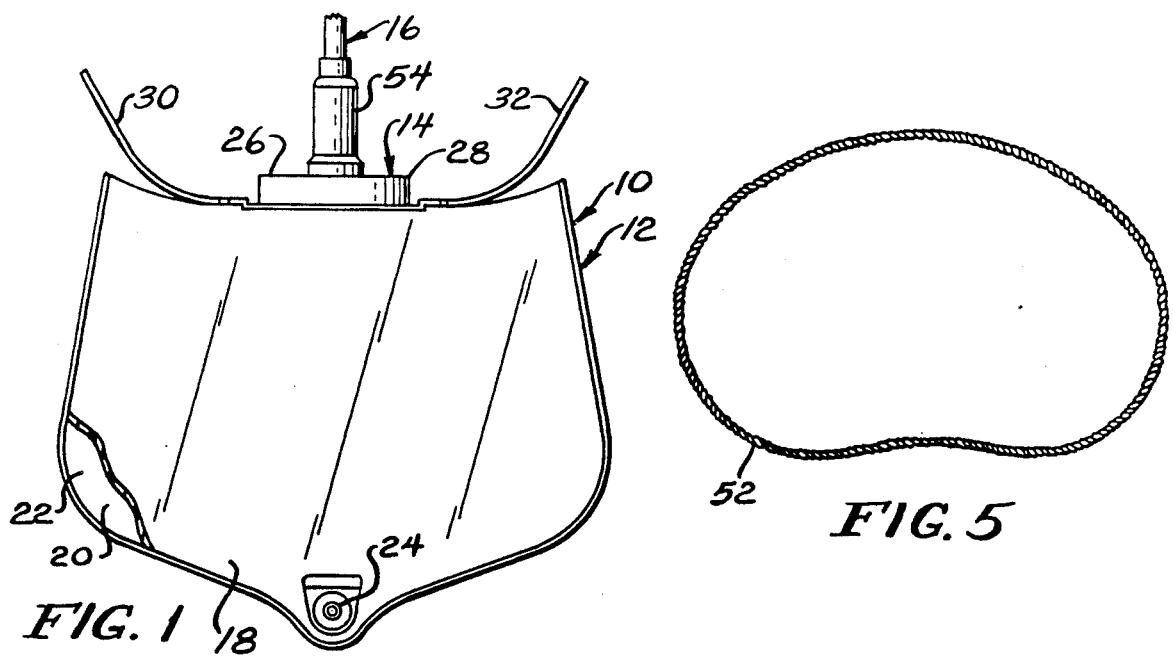
FIG. 1
FIG. 5
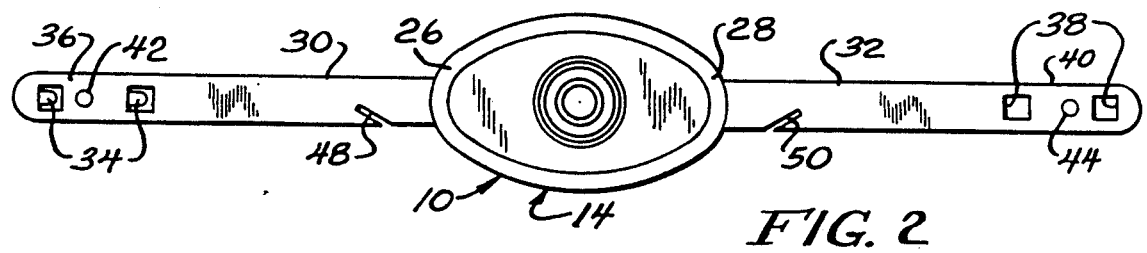
FIG. 2
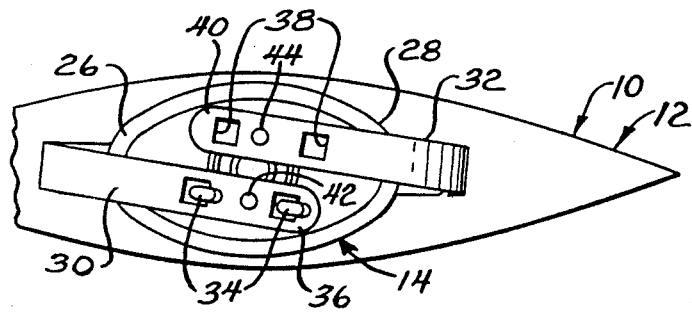
FIG. 3
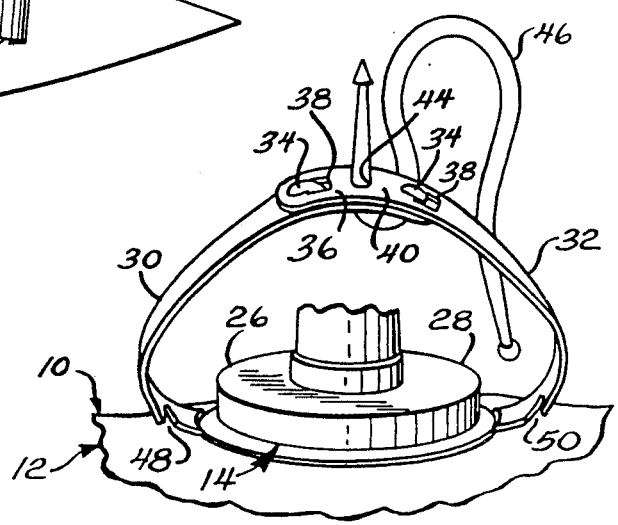
FIG. 4

LIQUID VALVE SYSTEM

This is a continuation of application Ser. No. 682,993, filed on Dec. 18, 1984, now abandoned, which is a divisional of Ser. No. 461,351, filed Jan. 27, 1983, now U.S. Pat. No. 4,526,576, issued July 2, 1985.

CROSS REFERENCE TO RELATED APPLICATION

This application is related to Ser. No. 461,350, filed Apr. 23, 1985, now U.S. Pat. No. 4,512,770, issued Apr. 23, 1985.

BACKGROUND OF THE INVENTION

The present invention relates to liquid drainage systems, and more particularly to systems for collection of urine.

Urine drainage systems have been known in the past. Such systems normally comprise a catheter, a drainage receptacle, and a drainage tube communicating between the catheter and receptacle. A distal end of the catheter is passed through the urethra of a patient until the catheter distal end is located in the bladder. Urine then drains through the catheter and drainage tube to the receptacle for collection therein.

It has been discovered that bacteria often accumulates in the collected urine. Hence, it is desirable to prevent the reflux of contaminated urine from the receptacle into the bladder where it might have a deleterious result to the patient. Hence, anti-reflux valves have been provided on the receptacle to prevent the reflux of urine from the receptacle when the receptacle is mishandled, such as when the receptacle is squeezed or placed on its back. However, the prior valves of this sort have required back flow of urine from the receptacle against the valve in order to actuate and close the valve when the receptacle is mishandled. Also, it is desirable to facilitate handling of the receptacle.

SUMMARY OF THE INVENTION

A principal feature of the present invention is the provision of an improved liquid drainage system of simplified construction.

The drainage system of the present invention comprises, a receptacle having a chamber for collection of liquid therein. The system has a housing secured to an upper portion of the receptacle and having a drip chamber, and opposed ends. The housing has a pair of opposed elongated flexible handle members extending from the housing ends.

A feature of the present invention is the provision of means for interlocking outer ends of the handle members together.

Another feature of the invention is that the interlocked handle members serve as a handle for the receptacle.

Still another feature of the invention is that the handle members each have a slit to receive a cord loop for hanging the receptacle from a suitable object.

Another feature of the invention is that the interlocked handle members have a pair of aligned apertures through which a hook member may be placed for hanging the receptacle from a suitable object.

Yet another feature of the invention is the provision of an anti-reflux valve at a lower portion of the drip chamber, with the housing having a vent with a bacteria filter and a channel communicating between the vent and an upper portion of the valve in order to vent the valve.

Still another feature of the invention is that the valve and accompanying seat are disposed at an angle relative to the horizontal such that the valve flexes to an open position when the receptacle is placed in an upright position, and flexes to a closed position when the receptacle is mishandled by placing it in a horizontal position.

A further feature of the invention is the provision of a collar extending peripherally around the seat and valve to limit and direct refluxing liquid against the valve with a force component perpendicular to the valve in order to close the valve.

Further features will become more fully apparent in the following description of the embodiments of this invention and from the appended claims.

DESCRIPTION OF THE DRAWINGS

In the drawings:

FIG. 1 is an elevational view of a liquid drainage system of the present invention;

FIG. 2 is an upper plan view illustrating a housing of the drainage system with opposed handle members;

FIG. 3 is a fragmentary upper plan view illustrating the handle members as flexed toward each other;

FIG. 4 is a fragmentary perspective view of the liquid drainage system illustrating the handle members secured to each other, and a hook member in place in the handle members;

FIG. 5 is a plan view of a cord loop for use on the handle members;

DESCRIPTION OF THE PREFERRED EMBODIMENTS

Figure 6:
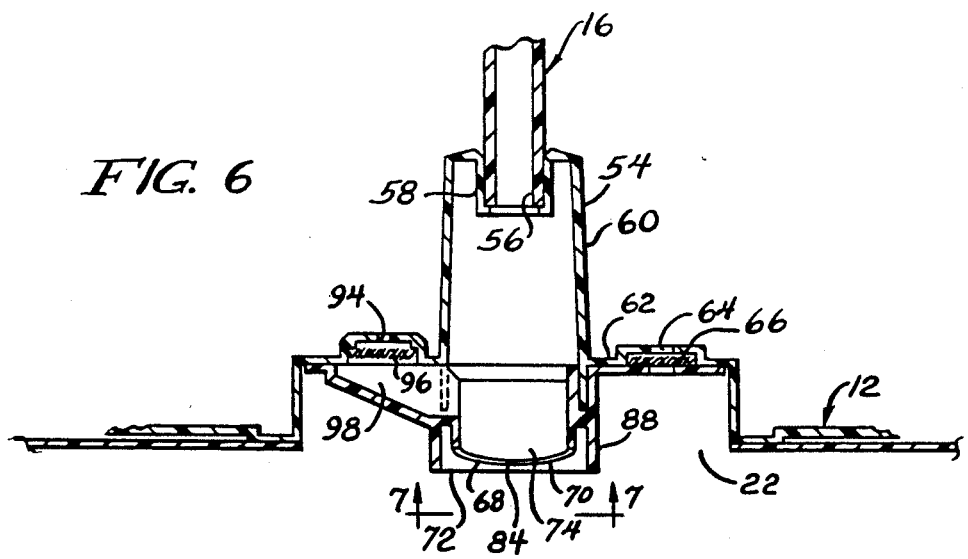
FIG. 6 is a fragmentary sectional view of the housing in slightly modified form for the liquid drainage system taken substantially as indicated along the line 6—6 of FIG. 3.

Referring now to FIGS. 1 and 2, there is shown a liquid drainage system generally designated 10 having a receptacle 12, a housing 14, and a drainage tube 16. The receptacle 12 has a front wall 18 of flexible plastic material, a back wall 20 of flexible plastic material, with the walls 18 and 20 being joined at their periphery in order to define a chamber 22 intermediate the front wall 18 and back wall 20. The receptacle 12 may have a tubular section 24 at a lower portion of the receptacle 12 in order to drain urine from the chamber 22.

The housing 14 may be constructed from a suitable flexible plastic material, such as 90 durometer polyvinyl chloride. The housing 14 is sealed to the front and back walls 18 and 20 peripherally around the housing 14 adjacent an upper portion of the front and back walls 18 and 20.

As shown, the housing 14 has opposed ends 26 and 28, and a pair of opposed elongated flexible handle members 30 and 32 extending from the ends 26 and 28 of the housing 14. The handle member 30 has a pair of spaced upstanding tabs 34 adjacent an outer end 36 of the handle member 30, and the handle member 32 has a pair of corresponding apertures 38 adjacent an outer end 40 of the handle member 32. The handle members 30 and 32 are illustrated as being flexed toward each other in FIG. 3. Next, with reference to FIG. 4, the tabs 34 may be placed in the apertures 38, and the handle members 30 and 32 are pulled in order to releasably interlock the handle members 30 and 32 together with the tabs 34 received in the apertures 38. In this configuration, the interlocked handle members 30 and 32 serve as a handle for carrying the receptacle 12.

With reference to FIGS. 2-4, the interlocked handle members 30 and 32 have a pair of aligned apertures 42 and 44 to receive a hook member 46 in order to hang the receptacle 12 from a suitable object, such as a bed rail. Alternatively, the handle members 30 and 32 have slots 48 and 50, respectively, adjacent the ends 26 and 28 of the housing 14 in order to receive a cord loop 52, as shown in FIG. 5, and hang the receptacle 12 from a suitable object, such as a bed rail, by the loop 52.

With reference to FIGS. 1 and 6, the housing 14 has a hollow drip chamber 54, with a downstream end 56 of the drainage tube 16 being received in an upper portion of the drip chamber 54. The drip chamber 54 has a drip tube 58 being spaced from an annular wall 60 of the drip chamber 54 in order to provide an air break for the incoming urine from the drainage tube 16, such that the drip chamber 54 prevents a continuous liquid path for possible retrograde migration of bacteria into the drainage tube 16.

The housing 14 has an upper wall 62 having a vent 64 communicating with the chamber 22 of the receptacle 12. The vent 64 has a bacteria filter 66 of known type to filter bacteria from the air passing through the vent 64 into the chamber 22 of the receptacle 12.

Figure 7:
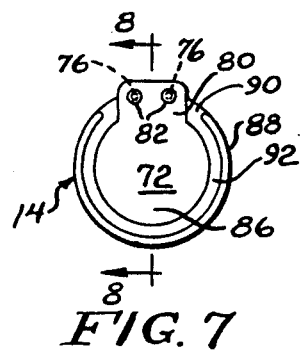
FIG. 7 is a lower plan view taken substantially as indicated along the line 7—7 of FIG. 6.
Figure 8:
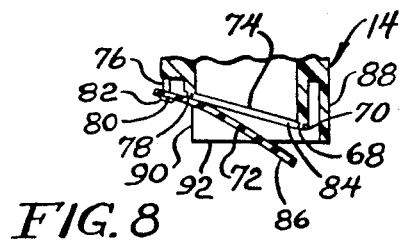
FIG. 8 is a fragmentary sectional view taken substantially as indicated along the line 8—8 of FIG. 7 and illustrating an anti-reflux valve in an open position.

With reference to FIGS. 6-8, the housing 14 has a lower annular edge 68 defining an annular valve seat 70 in a lower portion of the housing 14. The system 10 has an anti-reflex valve 72 comprising a sheet of suitable flexible material, such as rubber or silicone rubber, extending across an opening 74 defined by the valve seat 70, such that the valve 72 is sufficiently large to sealingly engage against the seat 70 peripherally around the edge 68. As shown, the seat 70 and valve 72 are disposed at an acute angle relative to the horizontal, such as in the range of 15 to 60 degrees relative to the horizontal when the receptacle 12 and drip chamber 54 are placed in an upright position. The housing 14 has a pair of downwardly projecting spaced pins 76 adjacent an upper portion 78 of the seat 70, with the pins 76 extending through an upper portion 80 of the valve 72. The pins 76 have enlarged outer ends 82 in order to hold the upper portion 80 of the valve 72 against the upper portion 78 of the seat 70. In a preferred form, as shown, a lower portion 84 of the seat 70 and a lower portion 86 of the valve 72 are located nearest the back wall 20 of the receptacle 12, and the upper portion 78 of the seat 70 and the upper portion 80 of the valve 72 are located nearest the front wall 18 of the receptacle 12.

Figure 9:
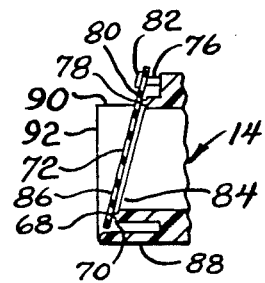
FIG. 9 is a fragmentary sectional view of the valve of FIG. 8 and illustrating the valve in a closed position.

In this configuration, as shown in FIG. 8, the lower portion 86 of the valve 72 automatically flexes away from the lower portion 84 of the seat 70 due to the action of gravity on the weight of the valve 72. Thus, when the receptacle 12 is placed in an upright position, the valve 72 automatically opens in order to facilitate passage of urine past the valve 72. However, with reference to FIG. 9, when the receptacle 12 is mishandled by placing it on its back, the lower portion 86 of the valve 72 automatically flexes against the lower portion 84 of the seat 70 due to the action of gravity on the weight of the valve 72. Thus, the valve 72 automatically closes when the receptacle 12 is mishandled by placing it on its back, and does not require the back flow of urine against the valves 72 in order to close the valve 72 and facilitate action of the valve 72.

With reference to FIGS. 6-8, the housing 14 has a collar or shield 88 depending below the valve 72 and seat 70, with the collar extending peripherally around the valve 72 and seat 70, and with the collar 88 having a cut-out 90 in the region of the upper portion 78 of the seat 70 and the upper portion 80 of the valve 72. The collar 88 limits and directs the urine which may reflux against the valve 72, such that the permitted reflux of urine passes through an opening 92 in the lower portion of the collar 88 or the cut-out 90, and such that the refluxing urine has a component of force normal to the valve 72 in order to more efficiently close the valve 72.

The housing 14 has a vent 94 in the upper wall 62, with a bacteria filter 96 of known type extending across the vent 94 to filter bacteria from the air passing through the vent 94. The housing 14 has a channel 98 extending from the vent 94 to an upper portion of the valve 72 in order to vent the valve 72 and facilitate passage of urine which may accumulate above the valve 72 through the valve 72.

The foregoing detailed description is given for clearness of understanding only, and no unnecessary limitations should be understood therefrom, as modifications will be obvious to those skilled in the art.

I claim:

1. A liquid drainage system, comprising:
   a receptacle having a front wall, a back wall, and a chamber for collection of liquid therein;
   a housing secured to an upper portion of the receptacle, said housing having a drip chamber, an annular wall in a lower portion of the drip chamber defining a valve seat, said seat being disposed at an acute angle relative to the horizontal when the receptacle is in an upright position;
   an anti-reflux valve comprising a sheet of flexible material having an upper portion and a lower portion and extending across said drip chamber such that the sheet is sufficiently large to engage against said seat peripherally around the drip chamber; and
   means for retaining an upper portion of the valve against an upper portion of the seat, said valve being sufficiently flexible such that a lower portion of the valve flexes away from the seat when the receptacle is placed in an upright position due to gravity in the absence of liquid adjacent said valve and seat, and said lower portion of the valve flexes against the seat when the receptacle is disposed in a horizontal position.

2. The system of claim 1 wherein the retaining means comprises a pair of spaced pins extending through the valve, and having enlarged outer ends to retain the valve in place.

3. The system of claim 1 wherein a lower portion of the valve and seat are located nearest a back wall of the receptacle, and in which an upper portion of the valve and seat are located nearest a front wall of the receptacle.

4. The system of claim 1 wherein the seat is disposed at an angle in the range of 15 to 60 degrees relative to the horizontal when the receptacle is placed in an upright position.

5. The system of claim 1 wherein said housing has a collar depending below said seat and valve.

6. The system of claim 5 wherein said collar extends peripherally around the valve and seat, with said collar having a cut-out located adjacent an upper portion of the valve and seat.

* * * * *